United States Patent [19]

Maurer et al.

[11] Patent Number: 4,678,776
[45] Date of Patent: Jul. 7, 1987

[54] PYRIDYL-THIONOPHOSPHORIC ACID ESTER USEFUL AS PESTICIDES

[75] Inventors: Fritz Maurer, Wuppertal; Bernard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 806,159

[22] Filed: Dec. 6, 1985

[30] Foreign Application Priority Data

Dec. 18, 1984 [DE] Fed. Rep. of Germany ....... 3446104

[51] Int. Cl.$^4$ .................. A61K 31/44; A61K 31/675; C07F 9/06
[52] U.S. Cl. .......................... 514/89; 546/25
[58] Field of Search ............................ 546/25; 514/89

[56] References Cited

U.S. PATENT DOCUMENTS 4,223,025  9/1980  Rigterink ........................ 546/25
4,224,318  9/1980  Pawloski ........................ 546/25

Primary Examiner—John M. Ford
Assistant Examiner—J. Richter
Attorney, Agent, or Firm—Sprung Horn Kramer & Woods

[57] ABSTRACT

Pesticidally active novel 2-pyridyl-thionophosphoric acid esters of the formula

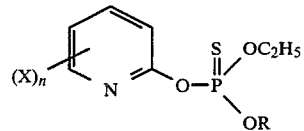

in which
R is i-propyl or sec.-butyl,
X each independently is halogen, and
n is 0, 2, 3 or 4.

13 Claims, No Drawings

PYRIDYL-THIONOPHOSPHORIC ACID ESTER USEFUL AS PESTICIDES

The invention relates to new 2-pyridyl-thionophosphoric acid esters, a process for their preparation and their use in pesticides, especially as insecticides, acaricides and nematicides.

It is known that certain thionophosphoric acid esters such as, for example, O,O-diethyl-O-(3,5,6-trichloro-2-pyridyl)-thionophosphoric acid ester, possess a pesticidal action (compare U.S. Pat. No. 3,244,586). However, the action, and duration of action, of these compounds are not always entirely satisfactory, especially in the case of certain insects.

There have now been found new 2-pyridyl-thionophosphoric acid esters of the formula (I)

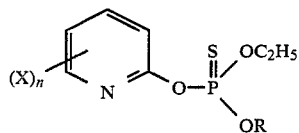    (I)

in which
R represents i-propyl or sec.-butyl,
X represents halogen, which may be identical or different and
n represents 0, 1, 2, 3 or 4.

Further, it has been found that the new 2-pyridylthionophosphoric acid esters of the formula (I) are obtained when 2-hydroxypyridines of the formula (II)

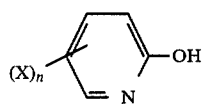    (II)

in which
X and n have the abovementioned meanings, or the corresponding alkali metal, alkaline earth metal or ammonium salts are reacted with halides of the formula (III)

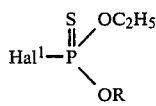    (III)

in which
R has the abovementioned meaning and
Hal$^1$ represents halogen, such as chlorine or bromine, if appropriate in the presence of an acid acceptor and, if appropriate, in the presence of a diluent.

The new 2-pyridyl-thionophosphoric acid esters of the formula (I) are exceptionally distinguished by a particularly high and long-lasting activity as pesticides, especially as insecticides, acaricides and nematicides.

The invention preferentially relates to compounds of the formula (I) in which
R represents i-propyl or sec.-butyl,
X represents halogen, which may be identical or different, such as, in particular, fluorine, chlorine or bromine and
n represents 0, 1, 2, 3 or 4.

Particularly preferred compounds of the formula (I) are those in which
R represents i-propyl or sec.-butyl,
X represents chlorine and/or bromine and
n represents 1, 2 or 3.

Very particularly preferred compounds of the formula (I) are those in which
R represents i-propyl or sec.-butyl,
X represents chlorine and
n represents 2 or 3.

If, for example, O-ethyl-O-i-propyl-thionophosphoric acid diester chloride and 2-hydroxy-pyridine are used as starting materials for the process according to the invention, the corresponding reaction can be outlined by the following equation:

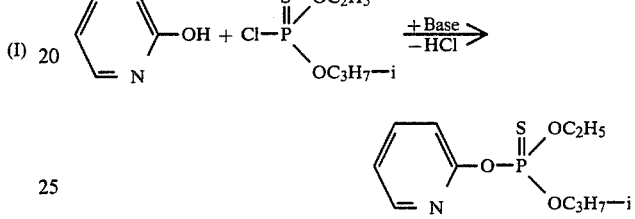

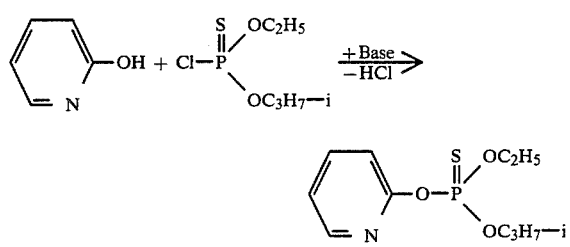

The 2-hydroxypyridines, or the corresponding alkali metal, alkaline earth metal or ammonium salts, to be employed as starting materials in the process according to the invention for the preparation of the new compounds of the formula (I) are defined by the formula (II). In this formula, X and n represent those radicals which have been mentioned above in the definition in formula (I). Preferably, the sodium, potassium, calcium or ammonium salts are employed as alkali metal, alkaline earth metal or ammonium salts.

The compounds of the formula (II) are known and/or can be prepared according to generally known processes and methods (compare, for example, U.S. Pat. Nos. 3,244,586 and 4,115,557).

As examples of the compounds of the formula (II) there may be mentioned: 2-hydroxy-pyridine, 6-chloro-, 6-bromo-, 6-fluoro-, 3,4-dichloro-, 3,5-dichloro-, 3,6-dichloro-, 3,5-dibromo-, 3,4,5-trichloro-, 3,5,6-trichloro-, 4,5,6-trichloro- and 3,4,5,6-tetrachloro-2-hydroxy-pyridine and the corresponding sodium, potassium, calcium and ammonium salts.

The halides also to be employed as starting materials are defined by the formula (III). In this formula, R represents those radicals which are mentioned in the definition in formula (I). Hal$^1$ in this formula represents halogen, such as, in particular, chlorine or bromine.

The compounds of the formula (III) are known.

As examples of the halides of the formula (III) there may be mentioned: O-ethyl-O-i-propyl and O-ethyl-O-sec.-butyl-thionophosphoric acid ester chloride and bromide.

The process according to the invention for the preparation of the new 2-pyridyl-thionophosphoric acid esters of the formula (I) is preferably carried out with use of diluents. Virtually all inert organic solvents can be used as the diluents.

These in particular include aliphatic and aromatic optionally halogenated hydrocarbons, such as pentane, hexane, heptane, cyclohexane, petroleum ether, petrol, ligroin, benzene, toluene, xylene, methylene chloride, ethylene chloride, chloroform, carbon tetrachloride, chlorobenzene, o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, as well as dimethylsulphoxide, tetramethylenesulphone and hexamethylphosphoric acid triamide.

The process can, where appropriate, be carried out in the presence of acid acceptors. All customary acidbinding agents may be used as the acid acceptors. Alkali metal carbonates, such as sodium carbonate and potassium carbonate, alkali metal hydrides, such as sodium hydride, and also aliphatic, aromatic or heterocyclic amines, for example triethylamine, trimethylamine, dimethylaniline, dimethylbenzylamine and pyridine, have proved particularly suitable.

The process according to the invention is in general carried out at temperatures between 0° C. and 100° C. A range between 20° C. and 80° C. is preferred. The reactions are in general carried out under normal pressure.

To carry out the process according to the invention, the starting materials are usually employed in approximately equimolar amounts. An excess of one or other reactants provides no essential advantages. The reaction is in general carried out in a suitable diluent, in the presence of an acid acceptor, and the reaction mixture is stirred for several hours at the requisite temperature. Thereafter, an organic solvent, for example toluene, is added and the organic phase is worked up in the usual manner by washing, drying and distilling off the solvent.

The new compounds are obtained in the form of oils which in part cannot be distilled without decomposition, but can be freed from the last volatile constituents by so-called "incipient distillation", i.e. by prolonged heating under reduced pressure at moderately elevated temperatures, and can be purified in this way. They are characterized by the refractive index.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.: From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus macrans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds according to the invention, of the formula (I), are distinguished by an excellent insecticidal and nematicidal activity. In particular, when used as soil insecticides they show an excellent action and particularly long-lasting activity against beetle larvae, such as, for example, Diabrotica spec.

The new compounds are accordingly particularly suitable for use in the long-lasting control of soil insects and nematodes.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents.

In the case of the use of water as an extender, organic solvents can, for example also be used as auxiliary solvents. As liquid solvents there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers there are suitable: for example ground natural minerals, such as kaolines, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices may be used in the formulations, such as gum arabic, polyvinyl alcohol and polyvinyl acetate, as well as natural phospholipids, such as cephalins and lecithins and synthetic phospholipids. Further additives can be mineral and vegetable oils.

It is possible to use colorants such as inorganic pigments, for example iron oxide, titanium oxide and Prussian blue, and organic dyestuffs, such as alizarin, azo and metal phthalocyanine dyestuffs, and trace nutrients, such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, mites, ticks, etc., in the sector of stock farming and animal raising, where, through combating the pests, better results, for example higher milk yields, higher weight, more attractive animal pelt, longer life, etc., can be achieved.

In these sectors, the active compounds according to the invention are used in a known manner, such as by external use in the form of, for example, dipping, spraying, pour-on and spot-on, and dusting.

The examples which follow are intended to illustrate the biological activity of the compounds according to the invention.

USE EXAMPLES

In the Use Examples which follow, the compound shown below is employed as a comparison compound:

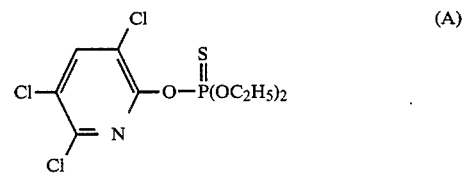

-continued
(from U.S. Pat. Specification No. 3,244,586)

EXAMPLE A

Test with *Lucilia cuprina* larvae (OP-resistant Goondiwindi strain)

Emulsifier:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 *Lucilia cuprina* res. larvae are introduced into a test tube which contains approx. 1 cm² of horse muscle and 0.5 ml of the preparation of active compound. After 24 hours, the degree of destruction is determined.

In this test, at, for example, an active compound concentration of 3 ppm, the compounds of, for example, preparation Examples (1) and (3) showed 100% destruction while, at the same concentration, the comparison compound (A) gave no destruction (0%).

EXAMPLES B AND C

Long-term action test/soil insects

Test insect: *Phorbia antiqua* maggots (Example B); *Diabrotica balteata* larvae (Example C)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (mg/liter) being decisive. The soil is filled into 5 liter pots and these are left to stand at 20° C.

After an interval of 2 weeks, and after prior renewed thorough mixing, soil samples of 250 cc are taken and the corresponding test insects are placed in the treated soil. After a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control. Result of Example B:

At an active compound concentration of 2.5 ppm, the comparison compound (A) showed a degree of destruction of 0% after 8 weeks, while the compounds of Examples 1, 2, 3 and 4, at the same active compound concentration, gave a degree of destruction of 100% after 8 weeks.

Result of Example C:
At an active compound concentration of 2.5 ppm, the comparison compound (A) showed a degree of destruction of 0% after 10 weeks, while the compounds of Examples 1, 3 and 4, at the same active compound concentration, gave a degree of destruction of 100% after 10 weeks.

PREPARATION EXAMPLES

EXAMPLE 1

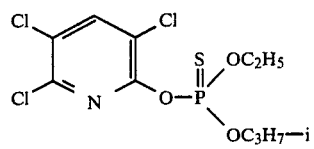

A mixture of 19.85 g (0.1 mole) of 2-hydroxy-3,5,6-trichloropyridine, 20.7 g (0.15 mole) of potassium carbonate, 20.2 g (0.1 mole) of O-ethyl-O-i-propyl-thionophosphoric acid diester chloride and 300 ml of acetonitrile is stirred for 6 hours at 50° C. It is then cooled to 20° C., 400 ml of toluene are added and the mixture is shaken twice with 200 ml of water at a time. The organic phase is separated off, dried over sodium sulphate and evaporated in vacuo. After incipient distillation at 80° C. in a high vacuum, 15.5 g (43% of theory) of O-ethyl-O-i-propyl-O-(3,5,6-trichloro-2-pyridyl)-thionophosphoric acid ester are recovered in the form of a pale brown oil of refractive index $n_D^{25}$:1.5280.

The following compounds of the formula (I) can be prepared analogously to Example 1:

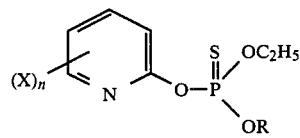

TABLE 1

| Example No. | R | $(X)_n$ | Refractive index |
|---|---|---|---|
| 2 | C₄H₉-sec. | 3,5,6-Cl₃ | $n_D^{25}$: 1.5246 |
| 3 | C₃H₇-i | 3,5-Cl₂ | $n_D^{25}$: 1.5248 |
| 4 | C₄H₉-sec. | 3,5-Cl₂ | $n_D^{25}$: 1.5197 |
| 5 | C₃H₇-i | 6-Cl | $n_D^{22}$: 1.5151 |
| 6 | C₄H₉-sec. | 6-Cl | $n_D^{22}$: 1.5143 |
| 7 | C₃H₇-i | 6-Br | |
| 8 | C₄H₉-sec. | 6-Br | |
| 9 | C₃H₇-i | 3,4,5,6-Cl₄ | |
| 10 | C₄H₉-sec. | 3,4,5,6-Cl₄ | |
| 11 | C₃H₇-i | 6-F | |
| 12 | C₄H₉-sec. | 6-F | |
| 13 | C₃H₇-i | n = 0 | |
| 14 | C₄H₉-sec. | n = 0 | |

It is understood that the specification and examples are illustrative but not limitative of the present invention and that other embodiments within the spirit and scope of the invention will suggest themselves to those skilled in the art.

We claim:
1. A 2-pyridyl-thionophosphoric acid ester of the formula

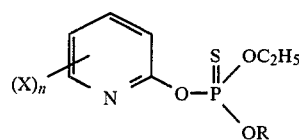

in which
R is i-propyl or sec.-butyl,
X chlorine is and
n is 0,1, 2, 3 or 4.

2. A compound according to claim 1, in which
X each independently is fluorine, chlorine or bromine.

3. A compound according to claim 1, in which
X is chlorine, and
n is 1, 2 or 3.

4. A compound according to claim 1, in which
X is chlorine, and
n is 2 or 3.

5. A compound according to claim 1, wherein such compound is O-ethyl-O-i-propyl-O-(3,5,6-trichloro-2-pyridyl)thionophosphoric acid ester of the formula

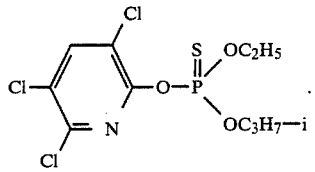

6. A oompound according to claim 1, wherein such compound is O-ethyl-O-i-propyl-O-(3,5-dichloro-2-pyridyl)-thionophosphoric acid ester of the formula

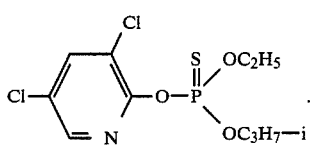

7. A compound according to claim 1, wherein such compound is O-ethyl-O-sec.-butyl-O-(3,5,6-trichloro-2-pyridyl)-thionophosphoric acid ester of the formula

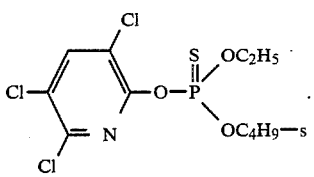

8. A compound according to claim 1, wherein such compound is O-ethyl-O-sec.-butyl-O-(3,5-dichloro-2-pyridyl)-thionophosphoric acid ester of the formula

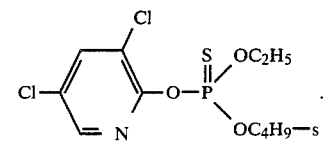

9. A compound according to claim 1, wherein such compound is O-ethyl-O-i-propyl-O-(6-chloro-2-pyridyl)-thionophosphoric acid ester of the formula

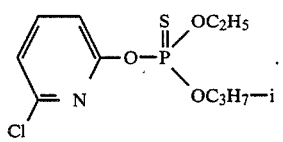

10. A compound according to claim 1, wherein such compound is O-ethyl-O-sec.-butyl-O-(6-chloro-2-pyridyl)-thionophosphoric acid ester of the formula

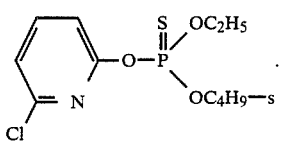

11. An insecticidal, acaricidal or nematicidal composition comprising an insecticidally, acaricidally or nematicidally effective amount of a compound according to claim 1 in admixture with a diluent.

12. A method of combating insects, acarids or nematodes which comprises applying thereto or to a habitat thereof an insecticidally, acaricidally or nematicidally effective amount of a compound according to claim 1.

13. The method according to claim 12, wherein such compound is
O-ethyl-O-i-propyl-O-(3,5,6-trichloro-2-pyridyl)-thionophosphoric acid ester,
O-ethyl-O-i-propyl-O-(3,5-dichloro-2-pyridyl)-thionophosphoric acid ester,
O-ethyl-O-sec.-butyl-O-(3,5,6-trichloro-2-pyridyl)-thionopnosphoric acid ester,
O-ethyl-O-sec.-butyl-O-(3,5-dichloro-2-pyridyl)-thionophosphoric acid ester,
O-ethyl-O-i-propyl-O-(6-chloro-2-pyridyl)-thionophosphic acid ester or
O-ethyl-O-sec.-butyl-O-(6-chloro-2-pyridyl)-thionophosphoric acid ester.

* * * * *